US008554695B2

(12) United States Patent
Irion et al.

(10) Patent No.: US 8,554,695 B2
(45) Date of Patent: Oct. 8, 2013

(54) COMPUTERIZED ANALYSIS OF GENETIC PROFILES VIA INTERNET PORTALS

(75) Inventors: Dawn Irion, Knoxville, TN (US); Tom Boyd, Knoxville, TN (US); Kevin David Jones, Knoxville, TN (US); Mark Boyd, Knoxville, TN (US); Michael Boyd, Knoxville, TN (US)

(73) Assignee: BioPet Vet Lab Inc., Knoxville, TN (US)

( * ) Notice: Subject to any disclaimer, the term of this patent is extended or adjusted under 35 U.S.C. 154(b) by 839 days.

(21) Appl. No.: 12/658,405

(22) Filed: Feb. 10, 2010

(65) Prior Publication Data

US 2010/0211532 A1 Aug. 19, 2010

Related U.S. Application Data

(60) Provisional application No. 61/207,628, filed on Feb. 13, 2009.

(51) Int. Cl.
*G06N 5/00* (2006.01)
(52) U.S. Cl.
USPC .............................. 706/11; 706/45

(58) Field of Classification Search
USPC ...................................... 706/11, 45
See application file for complete search history.

(56) References Cited

PUBLICATIONS

Perlin, Real-Time DNA Investigation, Proceedings of Promega's Sixteenth International Symposium on Human Identification, Nov. 4, 2005, pp. 1-18.*

* cited by examiner

*Primary Examiner* — Wilbert L Starks
(74) *Attorney, Agent, or Firm* — Law Office of Van R. Irion, PLLC

(57) ABSTRACT

A computer-implemented process and apparatus for storing, accessing, and comparing genetic profiles in a form suitable for amateur human analysis is provided. The process includes imputing and storing data that represent individual genetic profiles which have been created using conventional genetic analysis processes. The process and apparatus allow remote consumer access via the internet to genetic profiles owned by consumer which can then be compared against other genetic profiles according to a genetic profile comparison process selected from several available processes. The resulting output of the process is a summary of the genetic profile comparison which answers the question posed by the consumer.

20 Claims, 11 Drawing Sheets

Parentage Confirmation Process

Conventional Creation of a Genetic Profile

Personal Computer

The Internet

Consumer Actions

Identity Confirmation Process

Parentage Confirmation Process

Figure 8

Parentage Test Results

Parentage test results for DN Number: DI2917sf1

Date: 2/10/2009 11:52:00 AM

Result: Disqualified

Reason: Sire Disqualified

This analysis states that:

Puppy: Puppy09, DI2917sf1 is not the result of a mating between:

Dam: DAM02, DI2916d

Sire: Sire01, DI4000s

Analysis executed by:
Misty Harbor Chows

Why did I receive a "Disqualified" result, when I'm pretty sure the puppy should be qualified?

If the result indicates that the puppy is disqualified, and you believe it is in error, first check the DN numbers you entered to see if they are correct. If not, reenter your numbers and run the test again. You can run the parentage canalization as many times as you'd like.

If you are still getting a result of Disqualified and your numbers are correct, you may contact the BioPet Vet Lab and ask for an analyst to review the results with you.

After an analyst reviews your results, they may find what are known as "mutations" or "null alleles". These instances cannot be detected by the DNA World Pet Registries analysis tool. An analyst at BioPet has the authority to overwrite the Disqualified record and certify the puppy.

Figure 9a

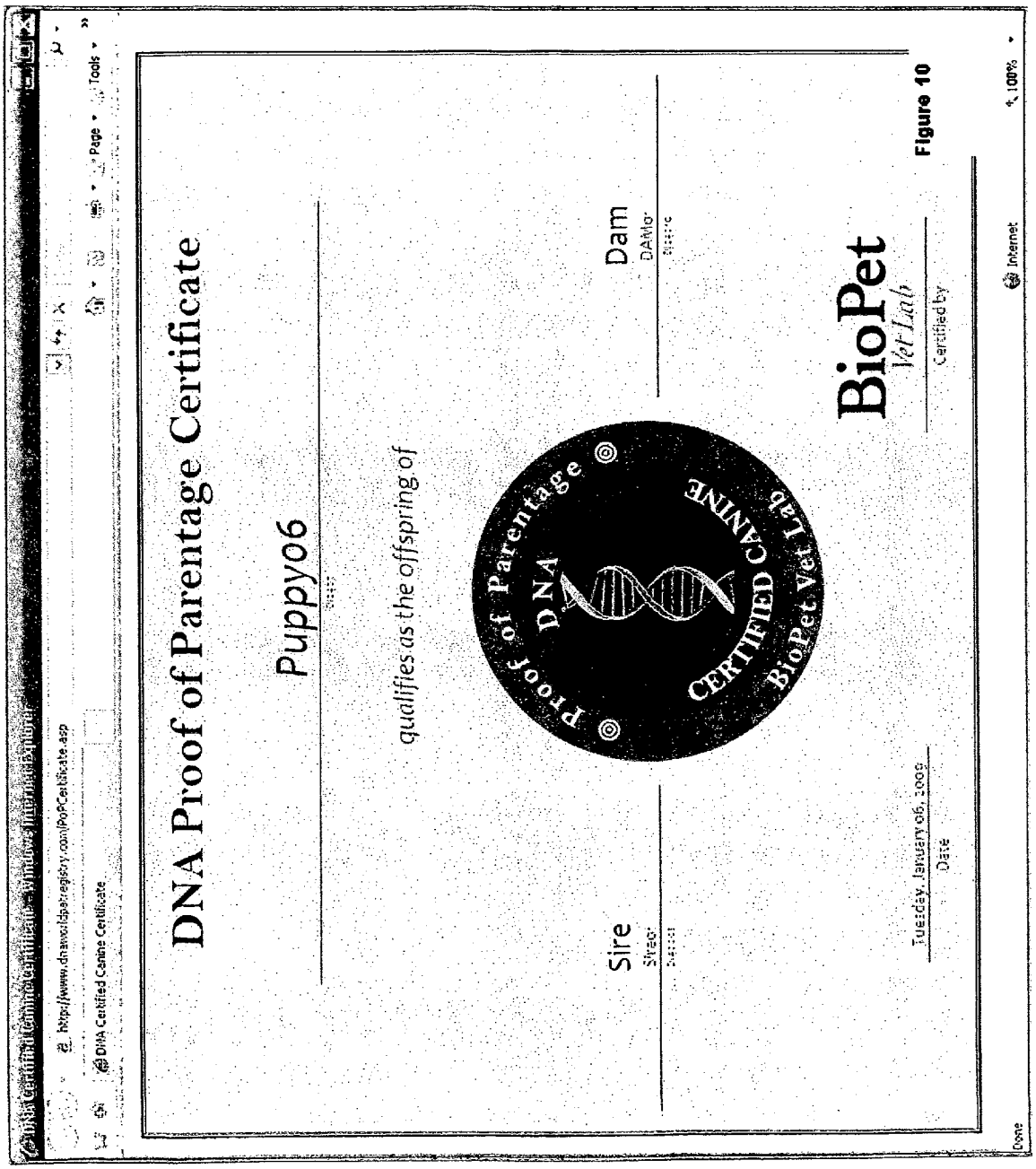

COMPUTERIZED ANALYSIS OF GENETIC PROFILES VIA INTERNET PORTALS

CROSS-REFERENCE TO RELATED APPLICATION

This application claims the benefit of U.S. Provisional Application No. 61/207,628 filed Feb. 13, 2009, which application is incorporated herein by reference.

BACKGROUND OF THE INVENTION

1. Field of the Invention

The present invention relates generally to computerized analysis of genetic information via an internet portal, and particularly, but not exclusively, to computerized systems and methods for the analysis of genetic profiles. More particularly, but not exclusively, the present invention relates to computerized systems for paternity and maternity testing using genetic profiles.

2. Definitions

Internet: The network of networks and gateways that use the TCP/IP suite of protocols.

Client computer: A computer which issues commands to the server.

Server: Any computer that performs a task at the command of another computer is a server. A Web server typically supports one or more clients.

World Wide Web (WWW or Web): The Internet's application that lets people seeking information on the Internet switch from server to server and database to database by clicking on highlighted words or phrases of interest (hyperlinks). An Internet WWW server supports clients and provides information. The Web can be considered as the Internet with all of the resources addressed as URLs and which uses HTML to display the information corresponding to URLs and provide a point-and-click interface to other URLs.

Universal Resource Locator (URL): A way to uniquely identify or address information on the Internet. Can be considered to be a Web document version of an e-mail address. They can be accessed with a Hyperlink. An example of a URL is "http://www.edpbiotech.com.html". A URL has four components. Starting from the left, the first specifies the protocol to use, separated from the rest of the locator by a ":". Next is the hostname or IP address of the target host; this is delimited by the "//" on the left and on the right by a "/" or optionally a ":". The port number is optional, and is delimited on the left from the hostname by a ":" and on the right by a "/". The fourth component is the actual file name or program name. In this example, the ".html" extension means that this is an HTML file.

HyperText Markup Language (HTML): HTML is the language used by Web servers to create and connect documents that are viewed by Web clients. HTML uses Hypertext documents. Other uses of Hypertext documents are described in U.S. Pat. No. 5,204,947, granted Apr. 20, 1993 to Bernstein et al.; U.S. Pat. No. 5,297,249, granted Mar. 22, 1994 to Bernstein et al.; U.S. Pat. No. 5,355,472, granted Oct. 11, 1994 to Lewis; all of which are assigned to International Business Machines Corporation, and which are incorporated by reference herein.

Hypertext Transfer Protocol (HTTP): HTTP is an example of a stateless protocol, which means that every request from a client to a server is treated independently. The server has no record of previous connections. At the beginning of a URL, "http:" indicates the file contains hyperlinks.

Internet Browser or Web Browser: A graphical interface tool that runs Internet protocols such as http, and displays results on the customers screen. The browser can act as an Internet tour guide, complete with pictorial desktops, directories and search tools used when a user "surfs" the Internet. In this application the Web browser is a client service which communicates with the World Wide Web.

Tissue: Any substance that contains material from which genetic information can be derived, resulting in a genetic profile, including but not limited to DNA, RNA, amino acids, single cells, portions of cells, multiple cells of the same type, or composite groups of cells of different types.

Genetic profile: A compilation of analyzed genetic data representing a tissue sample collected from a single person, animal, or plant, where specific values have been assigned for each allele analyzed.

Allele: An alternative form of a gene (one member of a pair) that is located at a specific position on a specific chromosome.

3. Description of Related Art

Genetic analysis is a multi step process. First a tissue sample is obtained, DNA is isolated, and the DNA is amplified using a process called PCR (Polymerase Chain Reaction). The PCR process results in millions to billions of copies of a specific segment of DNA. PCR can also be used to amplify RNA. PCR may or may not include the incorporation of a fluorescent tag within the segment. Amplified DNA must then be processed in one of several ways so as to create electronic data. There are many commercially available systems for processing PCR-amplified DNA products, including systems marketed by companies such as Promega Corporation and Applied Biosystems Incorporated (ABI). Once the amplified DNA has been processed and raw electronic data has been obtained, the data must then be analyzed to determine specific allele assignments for each DNA segment. Finally, the resulting genetic profile can be compared to other genetic profiles to verify identity, determine parentage, determine predisposition to disease, and for many other uses. These steps are described in more detail below.

There are two primary targets for the PCR process: STRs and SNPs. Both STRs and SNPs have been used extensively for various types of genetic analysis. Computer-implemented methods for discovering SNPs and determining genotypes are disclosed in, e.g., U.S. Pat. No. 5,858,659. While SNPs vary from individual to individual only in the sequence of the target DNA segment, STRs vary from individual to individual in the length and sequence of the target DNA segment. In either case the detectable differences between individuals in STR or SNP genetic profiles offer the opportunity to create a completely unique identification by DNA for each living creature on earth.

Fluorescently labeled STRs can be placed in a genetic analyzer that separates them on the basis of their size. Labeled SNPs can be detected by sequence specific primers of varying lengths which confer a size difference during PCR in the resulting DNA segment or by sequence specific probes such as affixed to a microarray. When dealing with segments of varying size, whether STR or SNP, conventional genetic analyzers use capillary electrophoresis to separate the segments by fragment size. A laser coupled with a photo-detector is then used to detect the amplified DNA segments of different sizes. An example of such a conventional system is the ABI 3730 Genetic Analyzer.

Typically, the output of a system such as the ABI3730 Genetic Analyzer is a raw data file for each sample which is stored electronically. Further analysis is required to convert the raw data to identifiable alleles for each DNA segment tested. The raw data can be imported into an analysis program such as ABI's GeneMapper. The GeneMapper program converts the raw data into an electropherogram which is a series of fluorescent peaks at varying sizes. By use of an internal standard common to every sample, the peaks are given a specific size, with one or two sizes or alleles detected at each DNA segment. A completed genetic profile consists of analyzed genetic data from a single tissue sample, where specific alleles have been assigned for each allele. At this point the genetic profile can be compared against other genetic profiles for several specific purposes.

One common use of genetic profiles is to confirm the parentage of an offspring.

For example, it is possible to identify the father of a child by testing the genetic of the mother, her child, and any number of potential fathers. Once tissue is obtained from the mother, the child, and the prospective fathers, genetic is isolated, processed, and analyzed to create genetic profiles for each individual. An analyst then compares the genetic profiles with each other. The genetic profile of the offspring must be a combination of the two actual parents. An allele in the offspring that cannot be attributed to one of the males excludes that male as a possible parent.

Another common use of genetic profiles is genetic matching. For example, a prized dog is stolen from a breeder's kennel. The breeder (breeder 1) suspects that another breeder (breeder 2) down the road now has her dog, but she can't prove it. She has tested her dog in the past and has his genetic profile stored. She obtains a tissue sample of the suspect dog and sends it to a lab for genetic analysis. The lab isolates and amplifies the genetic, as described above. The lab then creates a genetic profile for the suspect dog. Finally, an analyst compares the new genetic profile with the existing genetic profile. Identical genetic profiles serve as proof that the dog belongs to breeder 1.

Yet other uses of genetic profiles are trait detection and identifying predisposition to specific diseases. genetic segments that are amplified through the PCR process can be specified to genes that are associated with specific traits or diseases of interest. Typically, a consumer who wishes to know whether a subject has a certain trait or disease must submit a sample with personal information attached. Again, DNA is isolated and amplified, and a genetic profile is created. Again, an analyst must compare the genetic profile with profiles that are known to reflect association with the specific disease or trait of interest.

All of the current uses of genetic profiles require skilled analysts to perform comparisons of the genetic profiles after they have been produced. This requirement, that a skilled analyst perform all genetic profile comparisons, creates several limitations to the use of genetic analysis. Limited availability of skilled analysts creates delays in obtaining test results. Also, required use of skilled analysts for genetic profile comparisons reduces privacy for the consumer. Further, due to the current methods of genetic profile data storage skilled analysts often require new genetic profiles to be created prior to each comparison, even when an identical genetic profile has already been created for the individual being tested. This creates delays caused by unnecessary repetition in physical transport of tissue samples, data creation, and data processing. In other words, all the steps leading to production of a genetic profile for a given individual are unnecessarily repeated. Accordingly, there is a need for a computerized system that is accessible from anywhere in the world to store completed genetic profiles and to repeatedly perform specific genetic analyses at the direction of comparatively unskilled consumers, according to said consumer's specific inquiry, without the need to create new genetic profiles prior to each comparison.

SUMMARY OF THE INVENTION

The present invention provides a process and apparatus for storing and analyzing individual genetic profiles in a form that allows consumers to perform their own genetic profile comparison analysis, thus eliminating the requirement for a skilled analyst to perform genetic profile comparisons. The inventive process and apparatus also allows storage and repeated use of genetic profiles once they are created, eliminating the need for repeated tissue sample collection and repeated laboratory processing of samples. Furthermore, the novel process and apparatus allow consumers to quickly, privately, and remotely perform comparisons of genetic profiles at any time after said genetic profiles have been created.

The object of the invention, therefore, is to allow relatively unskilled consumers to perform genetic profile comparisons.

Another object of the invention is to allow remote access to the consumer's genetic profile data via the internet.

Yet another object of the invention is to provide perpetual storage and repeated use of electronic data representing genetic profiles.

These aspects, and others that will become apparent to the artisan upon review of the following description, can be accomplished through the following process: The process and apparatus disclosed accept as input electronic genetic profiles from a genetic analysis process. The genetic profiles are perpetually stored electronically for unlimited future genetic analysis. The consumer is informed electronically of the availability of the genetic profiles for analysis. The consumer accesses the genetic profiles via the Internet. The consumer selects from the genetic profiles available on a server, one or more genetic profiles to be analyzed. Depending upon the question the consumer would like answered, the consumer then selects one genetic comparison process from a plurality of available genetic profile comparison processes. The selected process compares the selected genetic profiles to determine the result, based upon the rules within the process selected. The result is then output to the consumer's client computer. The consumer can choose to make public the result of their genetic analysis or maintain privacy.

Comparison of selected genetic profiles is achieved by following pre-set rules for comparison of the selected genetic profiles, according to the comparison process selected. For example, when two genetic profiles are compared for the purpose of determining identity the inventive process begins by noting a value for a first allele on the first genetic profile. The process then compares said value against a value for the corresponding first allele of the second genetic profile. If the values are not identical, then the two genetic profiles do not represent the same individual. At this point the process outputs a result reflecting a negative match. If the values of the first allele are identical for both genetic profiles, then the process notes the value of the second allele for the first genetic profile and compares this value with the second allele of the second genetic profile. If the values are not identical, then the two genetic profiles do not represent the same individual. Again, at this point the process stops its analysis and outputs a result reflecting a negative match. If the values of the second allele are identical for both genetic profiles, then the process continues to the subsequent alleles, repeating said comparison until all alleles have been compared. If all alleles are identical for both genetic profiles, then the genetic profiles represent the same individual, and the process outputs a result identifying the individuals as the same.

In another example the consumer selects three genetic profiles and selects a parentage test as the comparison process. For this type of comparison the consumer must identify the genetic profile that reflects the offspring, and the genetic profile that represents two potential parents. The inventive process then notes the two values for each parent genetic profile for the first allele pair. From these values the four possible combinations of values in a resulting offspring, following classic Mendelian genetics, are noted. The process then compares the two values of the genetic profile of the first allele pair of the offspring with the four possible combinations created by the parents in question. If the two values of the offspring are not the same as any of the four possible combinations of values from the parents in question, then the process ends the analysis and outputs a result reflecting that the parents in question are not in fact the parents of the offspring in question. If the two values of the offspring are the same as any one of the four possible combinations of values from the parents in question, then the process notes the two values of the second allele of the genetic profiles of each parent in question, again creates four possible combinations representing possible values in an offspring for the second allele pair, and compares these combinations against the actual two values for the second allele of the offspring. This process is repeated for each allele pair. If any allele results in two values of the offspring that do not match any one of the four possible combinations of values from the parents for that allele pair, then the inventive process stops the analysis and outputs a result reflecting that the offspring is not the offspring of the two parents in question. If all the offspring's allele pairs represent values that match any one of the combinations of values from the parents in question for the given allele pairs, then the process outputs a result confirming that the offspring is in fact the offspring of the parents in question.

In another example the consumer can select more than one genetic profile to compare for identity confirmation against a known genetic profile. Similarly, the consumer can also select more than one genetic profile representing potential parents using the confirmation of parentage process, as long as the genetic profiles of the potential known parents are available and the genetic profile of the offspring is available. In the case of multiple identity confirmation comparisons, the inventive process simply completes the steps of the comparison described above for the first potential genetic profile, then repeats the steps for the next selected genetic profile, comparing each sequential genetic profile against the genetic profile of the one known individual. In the case of testing multiple potential parents against a known offspring and one known parent, the inventive process follows the steps described above for parentage genetic profile comparisons, comparing each potential second parent in sequence and providing results for each potential parent comparison in sequence.

In addition to the examples given for the inventive process steps, the inventive process includes steps for dealing with incomplete or incorrect data, which is sometimes included in genetic profiles. Due to uncertainty in the biomolecular procedures used when producing raw data for genetic profiles, often raw data derived from genetic analysis procedures will not be conclusive regarding values for specific alleles. Therefore genetic profiles occasionally include one or more alleles that have no value assigned. Additionally, genetic profiles occasionally include values for specific alleles that may or may not be correctly identified. When the inventive process encounters an allele that is missing a value it simply skips that allele and moves on to the next allele in sequence. The inventive process may also include instructions to include comparison of a specific allele, but to continue the comparison even if a negative result is reached for that allele. Such instructions may be included to prevent false negative results being reported due to raw data that led to assignment of values for a specific allele where the assignment of said value was not certain.

It is to be understood that both the foregoing general description and the following detailed description provide embodiments of the invention and are intended to provide an overview or framework of understanding the nature and character of the invention as it is claimed.

BRIEF DESCRIPTION OF THE SEVERAL DRAWINGS

FIG. 8 is a depiction of an exemplary web page of the present invention showing consumer options for selecting from available genetic profiles and selecting from available comparison processes.

FIGS. 9A & 9B are depictions of exemplary web pages of the present invention showing output of negative and positive results of an exemplary genetic profile comparison.

FIG. 10 is a depiction of an exemplary web page of the present invention showing an exemplary printable certificate verifying the result of a given genetic profile comparison.

DETAILED DESCRIPTION OF THE PREFERRED EMBODIMENTS

Figure 1:
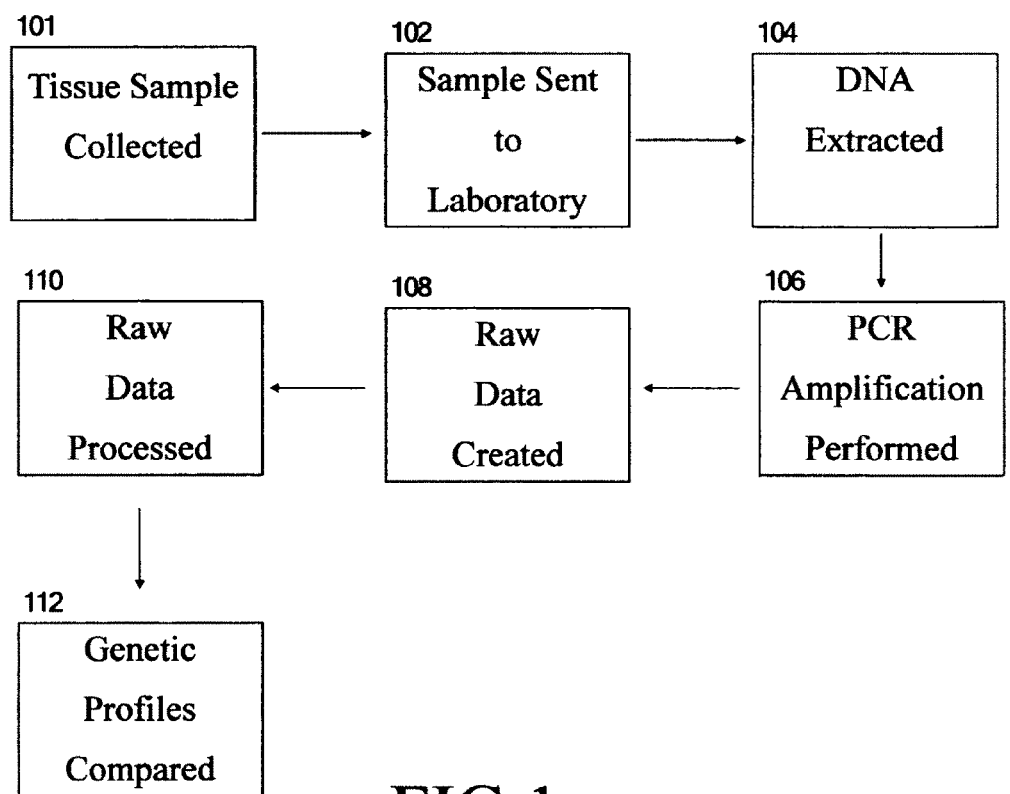
FIG. 1 is a block diagram representing an overview of the processes involved in genetic analysis.

This detailed description is represented largely in terms of processes and symbolic representations of operations by conventional computer components, including a processor, memory storage devices for the processor, connected display devices, and input devices. Furthermore, these processes and operations may utilize conventional computer components in a heterogeneous distributed computing environment, including remote file servers, computer servers, and memory storage devices. Each of these conventional distributed computing components is accessible by the processor via a communication network.

The processes and operations performed by the computer include the manipulation of signals by a processor or remote server and the maintenance of these signals within data structures resident in one or more of the local or remote memory storage devices. Such data structures impose a physical organization upon the collection of data stored within a memory storage device and represent specific electrical or magnetic elements. These symbolic representations are the means used by those skilled in the art of computer programming and computer construction to most effectively convey teachings and discoveries to others skilled in the art.

For the purposes of this discussion, a process is generally conceived to be a sequence of computer-executed steps leading to a desired result. These steps generally require physical manipulations of physical quantities. Usually, though not necessarily, these quantities take the form of electrical, magnetic, or optical signals capable of being stored, transferred, combined, compared, or otherwise manipulated. It is conventional for those skilled in the art to refer to these signals as bits, bytes, words, values, elements, symbols, characters, terms, numbers, points, records, objects, images, files or the like. It should be kept in mind, however, that these and similar terms should be associated with appropriate physical quantities for computer operations, and that these terms are merely conventional labels applied to physical quantities that exist within and during operation of the computer.

It should also be understood that manipulations within the computer are often referred to in terms such as adding, calling, comparing, receiving, sending, transferring, transmitting, etc. which are often associated with manual operations performed by a human operator. The operations described herein are machine operations performed in conjunction with various input provided by a human operator or user that interacts with the computer.

Referring now to the drawings, in which like numerals represent like elements throughout the several figures, aspects of the present invention and the preferred operating environment will be described.

FIG. 1 is a block diagram representing the general steps taken to perform a complete genetic analysis. At step 101 a tissue sample is collected. Tissue samples include any tissue that contains DNA, RNA, amino acids, or other genetic material, taken from a single individual. Tissue samples include, but are not limited to hair, blood, skin, or other cell, cells, or portions of cells, reflecting a single type of cell or a mixture of several types of cells. It is understood that DNA is only an exemplary genetic material. Any material from which genetic information and can be derived, leading to a genetic profile is within the scope and spirit of the present invention. Because DNA does not degrade quickly after death, tissue samples can be living or dead at the time they are collected. Tissue samples can be stored for long periods of time without significant DNA degradation. Cheek epithelial cells are commonly collected for genetic analysis.

At step 102 the tissue samples are physically transported to the site where DNA extraction is to take place. Typically this location is the same as the location where further processing will be performed. Because DNA does not quickly degrade in dead tissue, the method or conditions of transportation is not critical to successful DNA isolation. Tissue samples are typically mailed to laboratories for DNA extraction via standard US post.

At step 104 the DNA is extracted from the tissue. Extraction involves liberating the DNA from cell nuclei and separating the DNA from other tissue debris. Several processes for successfully extracting DNA are well known in the art.

At step 106 the DNA is amplified via the PCR process. The PCR process results in millions to billions of copies of a specific segment of DNA. PCR may or may not include the incorporation of a fluorescent tag within the segment. PCR is also well known to one skilled in the art of genetic analysis.

At step 108 the amplified DNA is processed using one of several possible methods and apparatus, to generate raw data. For example, fluorescently labeled PCR-amplified DNA can be placed in a genetic analyzer that separates them on the basis of their size. Conventional genetic analyzers often use capillary electrophoresis to separate the segments by fragment size. A laser coupled with a photo-detector is then used to detect the amplified DNA segments of different sizes. An example of such a conventional system is the ABI 3730 Genetic Analyzer. Typically, the output of a system such as the ABI3730 Genetic Analyzer is a raw data file for each sample which is stored electronically.

At step 110 the raw electronic data is processed to determine numerical values for each allele that has been amplified. Software and procedures used for this step vary, but all result in a genetic profile (GP) that consists of specific values assigned for each allele that has been amplified via the PCR process. It should be understood that allele values assigned may be non-numerical values, yet remain within the scope of the present inventions. Other symbolic values, including but not limited to letters for example, can be used to assign specific values to alleles.

For genetic profiles to be of value they must be compared to other Genetic profiles 112. The process of automatically comparing genetic profiles 112 for various purposes, after they are generated, is the focus of this application. Therefore, step 112 is further discussed and expanded upon in FIGS. 4, 5, and 6.

Figure 2:
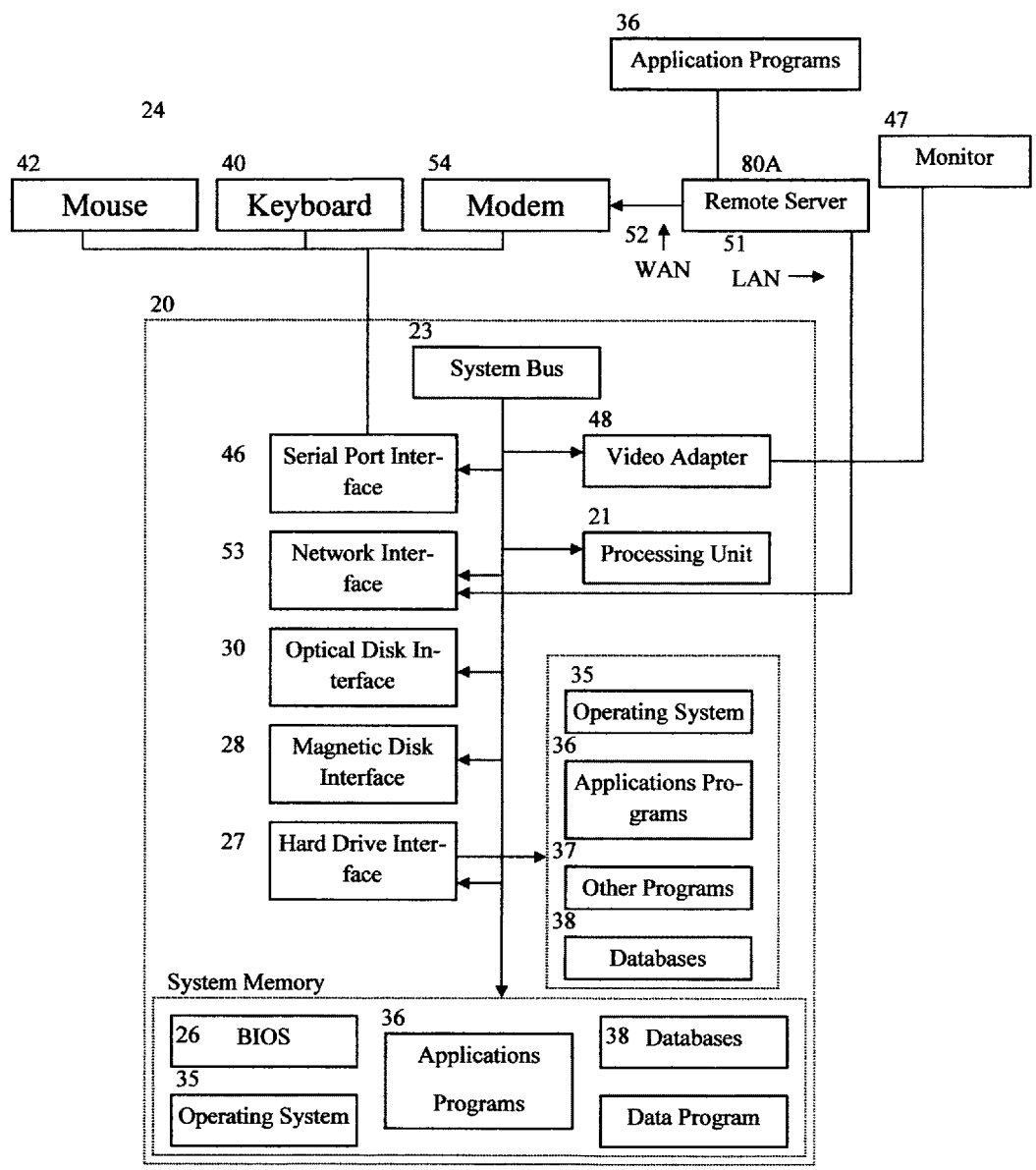
FIG. 2 is a functional block diagram of a computer that provides a portion of the operating environment for an exemplary embodiment of the invention.

FIG. 2 and the following discussion are intended to provide a brief general description of a suitable computing environment in which the invention may be implemented. While the invention will be described in the general context of a program module, such as a software application, that runs on an operating system in conjunction with a computer, those skilled in the art will recognize that the invention also may be implemented in combination with other program modules.

Generally, program modules include routines, programs, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, minicomputers, mainframe computers, and the like. The invention may also be practiced in distributed computing environments where tasks are performed by remote processing devices that are linked through a communications network. In a distributed computing environment, program modules and data may be located in both local and remote memory storage devices.

With reference to FIG. 2, an exemplary system for implementing the invention includes a conventional personal computer 20, including a processing unit 21, a system memory 22, and a system bus 23 that couples the system memory to the processing unit 21. The system memory 22 includes read only memory (ROM) 24 and random access memory (RAM) 25. A basic input/output system 26 (BIOS), containing the basic routines that help to transfer information between elements within the personal computer 20, such as during start-up, is stored in ROM 24. The personal computer 20 further includes a hard disk drive 27, a magnetic disk drive 28, e.g., to read from or write to a removable disk, and an optical disk drive 30, e.g., for reading a CD-ROM disk or to read from or write to other optical media. The hard disk drive 27, magnetic disk drive 28, and optical disk drive 30 are connected to the system bus 23 by a hard disk drive interface, a magnetic disk drive interface, and an optical drive interlace, respectively. The drives and their associated computer-readable media provide nonvolatile storage for the personal computer 20. Although the description of computer-readable media above refers to a hard disk, a removable magnetic disk and a CD-ROM disk, it should be appreciated by those skilled in the art that other types of media which are readable by a computer, such as magnetic cassettes, flash memory cards, digital video disks, Bernoulli cartridges, and the lace, may also be used in the exemplary operating environment.

A number of program modules may be stored in the drives and RAM 25, including an operating system 35, one or more program modules 36, other program modules, such as the present invention, system databases 37, and program data 38. A user may enter commands and information into the personal computer 20 through a keyboard 40 and pointing device, such as a mouse 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a game port or a universal serial bus (USB). A monitor 47 or other type of display device is also connected to the system bus 23 via an interface, such as a video adapter 48. In addition to the monitor, personal computers typically include other peripheral output devices (not shown), such as speakers or printers.

Figure 3:
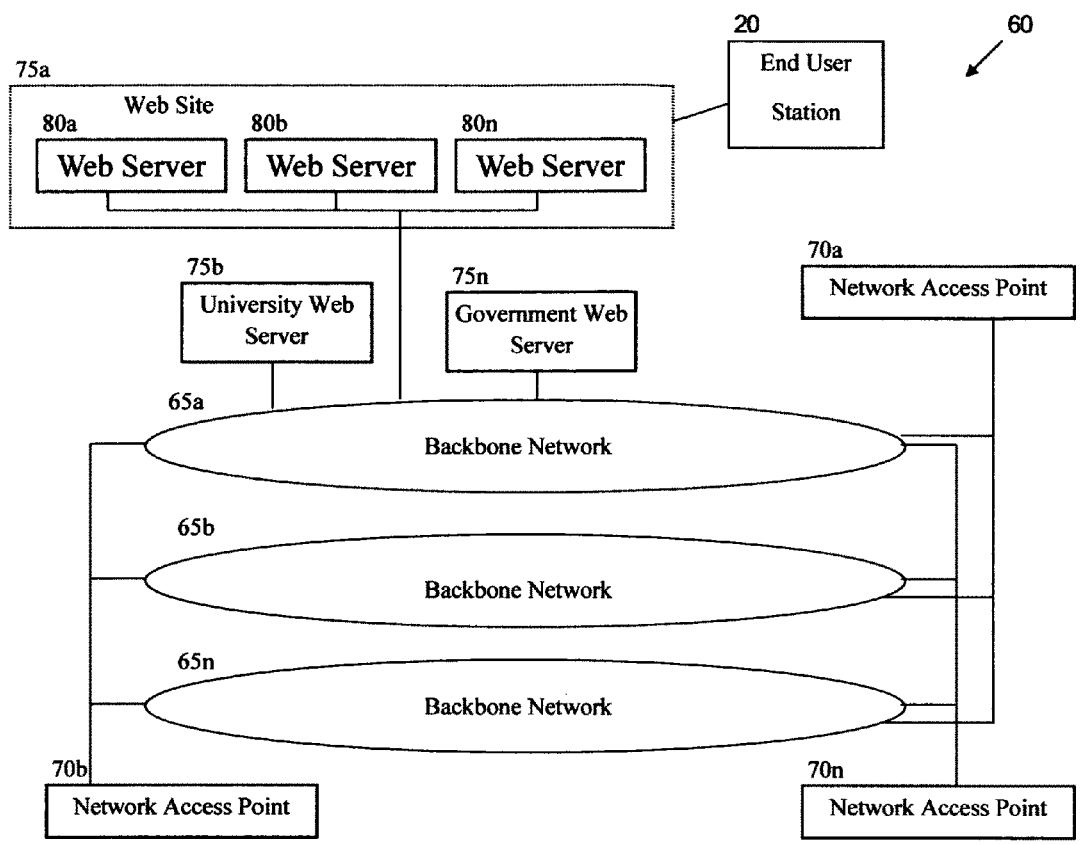
FIG. 3 is a functional block diagram of the Internet representing a portion of the operating environment of an exemplary embodiment of the present invention.

The personal computer 20 may operate in a networked environment using logical connections to one or more remote computers. The remote computer may be a server, such as an Internet-based remote server 80a, a router, a peer device or other common network node, and typically includes many or all of the elements described relative to the personal computer 20, although only a memory storage device 50 has been illustrated in FIG. 2. The logical connections depicted in FIG. 2 include a local area network (LAN) and a wide area network (WAN). Such networking environments are commonplace in offices, enterprise-wide computer networks, intranets and the Internet, which is illustrated in FIG. 3. It will be appreciated that the network connections shown are exemplary and other means of establishing a communications link between the computers may be used.

FIG. 3 is a functional block diagram of the Internet 60, a distributed electronic computing network that provides a portion of the operating environment for the preferred embodiment of the present invention. The Internet has in recent years become a mainstream commercial communication resource. E-mail and remote access to computer servers are currently widely used tools for reaching customers. The participants in the Internet are a wide variety of machines, organizations, and individuals, all able to communicate and share information. Physically, the Internet is an interconnected collection of thousands of computer networks, tens of thousands of computers, and tens of millions of individual stations operated by end users. The user of the preferred embodiment of the present invention is preferably such an end-user. As is well known to those skilled in the art, to access an Internet site, an end user need only transmit the site's universal resource locator (URL) created in accordance with the standardized Domain Name System (DNS).

The Internet 60 includes a plurality of backbone networks 65a through 65n. These backbone networks form an international grid of high-speed, high-capacity data communication lines interconnecting a number of massive computers that serve as large-scale processing points or nodes. The backbone networks 65 are interconnected with each other through a plurality of network access points 70a through 70n. These network access points are interfaces through which information is communicated from one backbone network to another. The configuration and operation of the Internet backbone is well known to those skilled in the art and will not be further described herein.

The Internet 60 includes a plurality of Internet sites 75a through 75n. These Internet sites are generally operated by corporations, universities, and governmental organizations. Each Internet site may include one or more repositories of information and resources that may be accessed over the Internet. Each Internet site, as represented by the Internet site 75a, may include a plurality of web servers 80a through 80n. Each of these web servers may provide "home pages" to be visited, files to be read or downloaded, applications to be shared, and the like.

As stated above, the personal computer 20, illustrated in FIG. 2, is an end user station 20a connected to the Internet 60, illustrated in FIG. 3. As will be understood from the following discussion, the present invention provides for interaction between Internet-based components of the present invention maintained on the Internet-based Genetic profile comparison process server 80a (FIG. 3) with remote components of the present invention operated on the local computer 20 (FIGS. 2 and 3).

Figure 4:
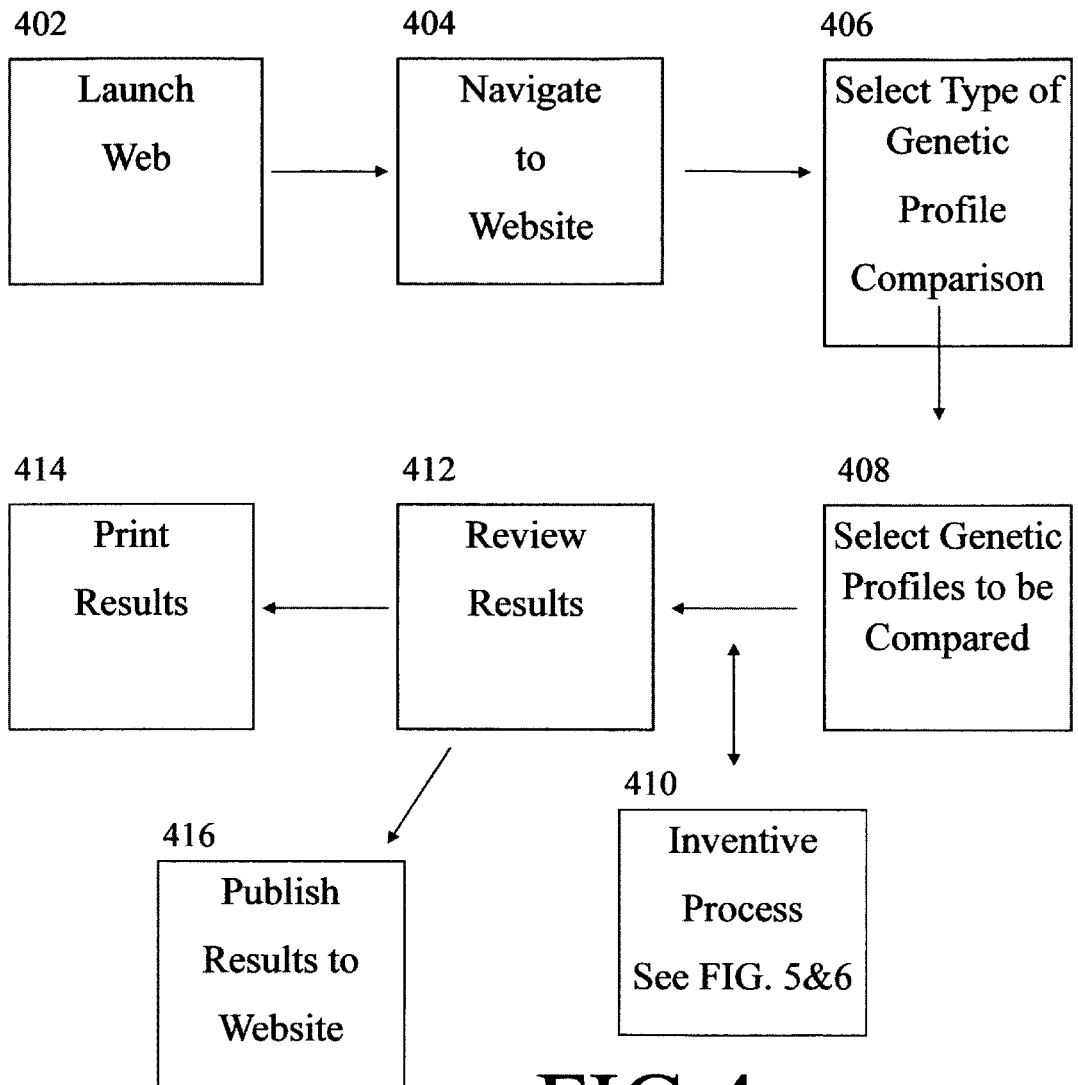
FIG. 4 is flow chart representing an exemplary embodiment of the steps taken by a consumer implementing the inventive process.
Figure 5:
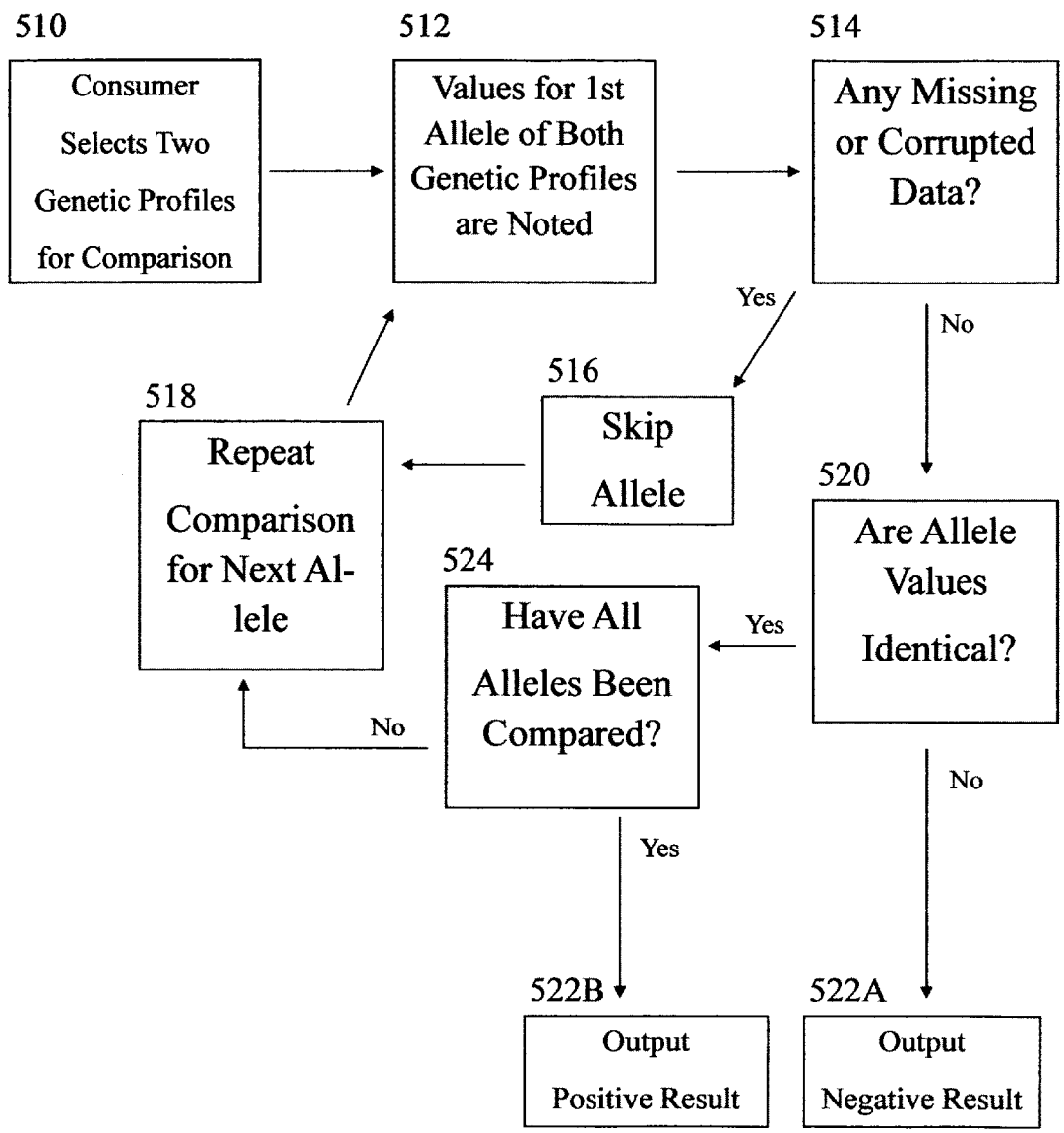
FIG. 5 is a flow chart representing an exemplary embodiment of the steps taken by the inventive process in performing a comparison of two genetic profiles for confirmation of identity.
Figure 6:
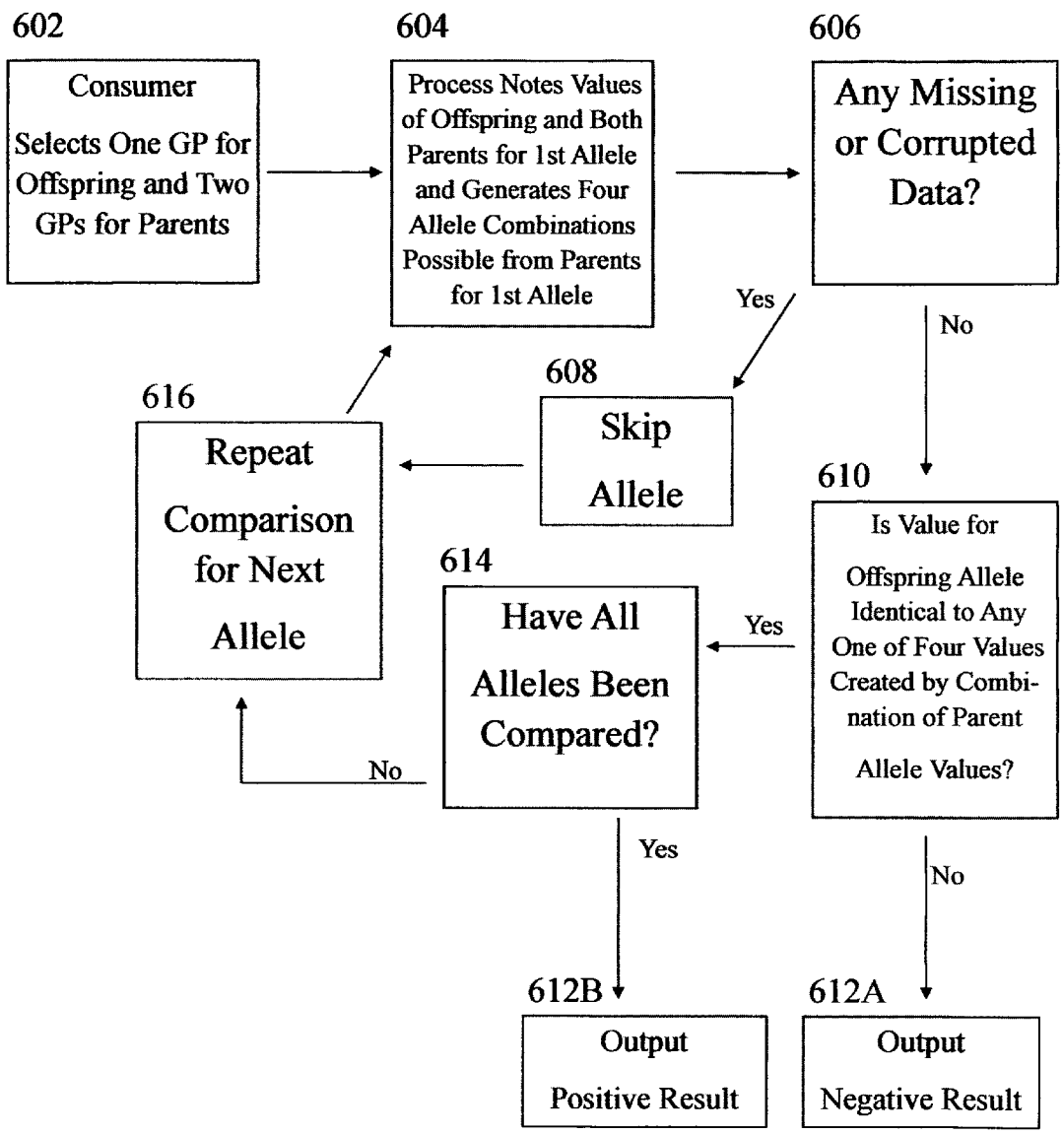
FIG. 6 is a flow chart representing an exemplary embodiment of the steps taken by the inventive process in performing a comparison of three genetic profiles for confirmation of parentage.

As discussed above, this invention is directed to a process and apparatus for remote comparison of genetic profiles. Referring now to FIGS. 4, 5, and 6, the genetic profile comparison process of the present invention includes several genetic profile comparison Programs (DPCP) available for use by the consumer via an Internet-based genetic profile comparison web site (WS). The present invention is best illustrated by showing an exemplary embodiment of how the inventive process allows a consumer to test parentage of a particular subject via genetic profile comparison, using an exemplary WS.

Figure 7:
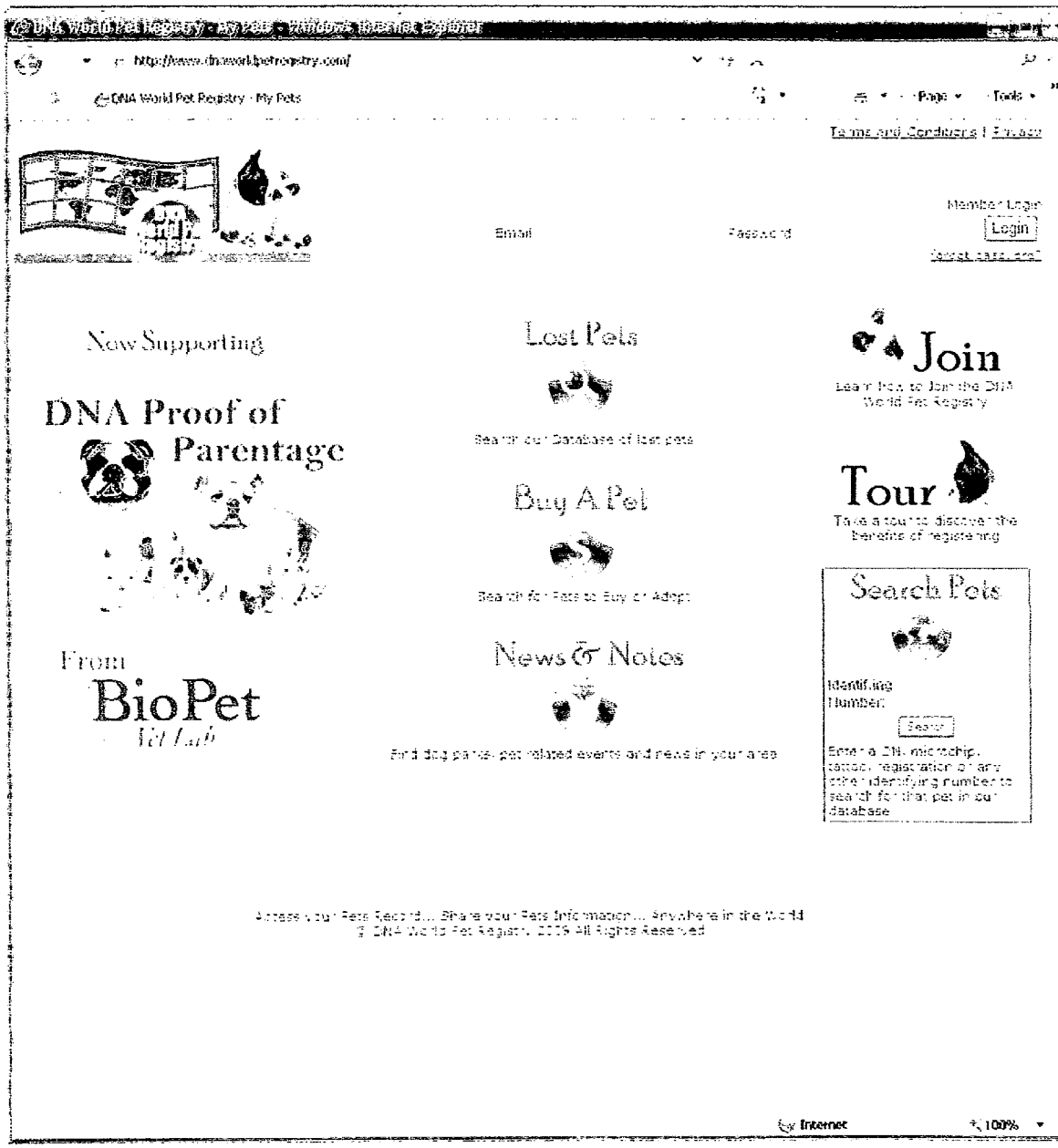
FIG. 7 is a depiction of an exemplary home page of the present invention.
Figure 8:
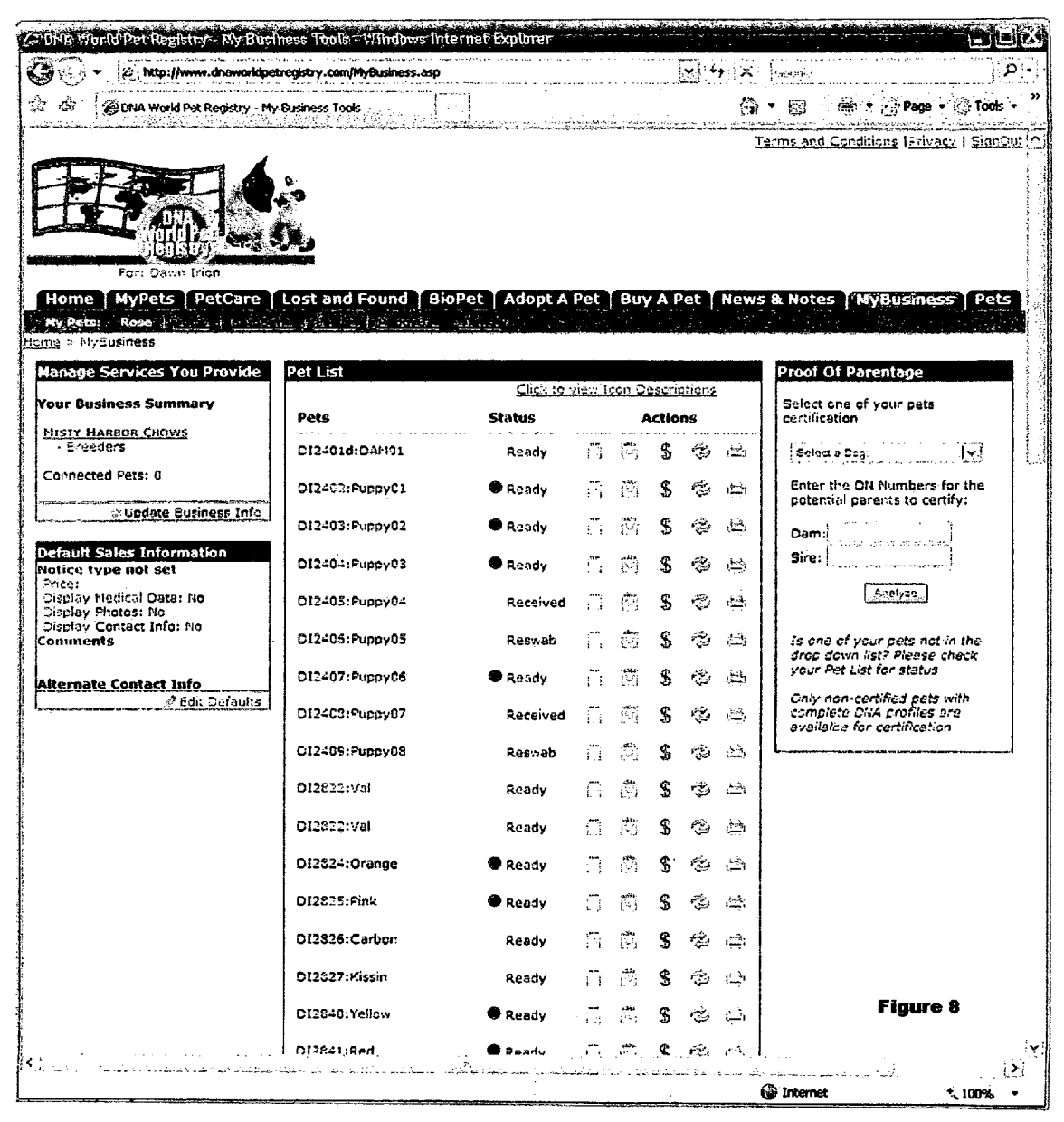
Figure 9B:
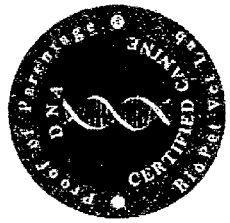

As an expansion of step 112 from FIG. 1, FIG. 4 is a flow chart representing an exemplary embodiment of the steps taken by a consumer implementing the inventive process. Upon launching a web browser 402 and navigating 404 to the URL http://www.geneticworldpetregistry.com the home page appears on the consumer's personal computer. An exemplary web page representing this step is shown in FIG. 7. Depending upon the question the consumer would like answered, the consumer then selects one genetic profile comparison process from a plurality of available genetic profile comparison processes 406. The consumer then selects from the genetic profiles available on a server, two or more genetic profiles to be analyzed 408. An exemplary web page representing steps 406 and 408 is shown in FIG. 8. The selected process then compares the selected genetic profiles to determine the result, based upon the rules within the process selected 410. Exemplary processes representing common forms of step 410 are described in FIGS. 5 and 6. The result is then output to the consumer's client computer 412. An exemplary web page representing this step is shown in FIG. 9. The consumer then chooses the make the result of their genetic analysis public 416, or maintain privacy. In either case the consumer can print a certificate verifying the result of their genetic analysis. An example of such a certificate is shown in FIG. 10.

The server hosting such a web site can, optionally, create an account for each consumer, thereby allowing private information to be associated and accessed according to the server's account access processes. Large numbers of genetic profiles can be stored on the server and may be accessed by or sequestered from individual consumers according to the server's access protocols. Also, consumers may add information to be associated with individual genetic profiles for additional identification or other purposes, again according to the server's account access protocols. Additional information that can be associated with a given genetic profile includes, but is not limited to identifying marks, appearance, photographs, medical history, and personal notes.

Upon creation of a new genetic profile a data set including all allele data for that tissue sample is created. This data set is read into an array, analyzed for accuracy and mapped to a numeric set of fields in the program's database. The data is then written to the database, and associated with the consumer records, discussed above. Further, once a genetic profile has been stored in a database it is stored indefinitely. The inventive process disclosed herein allows repeated comparison of stored genetic profiles, in perpetuity.

Expanding upon step 410 from FIG. 4, FIG. 5 is a flow chart representing an exemplary embodiment of the steps taken by the inventive process in performing a comparison of two genetic profiles for confirmation of identity. Beginning at step 510, which corresponds to step 408 of FIG. 4, the consumer selects two genetic profiles to be compared. The inventive process begins by noting a numerical value for a first allele on the both genetic profiles to be compared 512. The process then determines if the values noted represent missing or corrupted or erroneous data 514. In other words the process determines whether the values from the first allele for both genetic profiles are valid numerical values representing actual allele values, as opposed to null values or values that are outside of valid allele ranges. If the values are determined to be null or corrupted or erroneous, then the process skips the allele being compared at that time 516, and repeats the process for the next allele 518, which returns the process to step 512. If the process determines that the data for an allele is present and not erroneous, then it determines if the values for that allele are identical for both genetic profiles being compared 520. If the values are not identical then the process ends the analysis and a result is output to the consumer's computer reflecting that the two genetic profiles are not identical 522A.

If two tissue samples are taken from the same individual, all alleles will reflect exactly the same numerical values in two genetic profiles created from the tissue samples. This is true regardless of what lab performs the genetic analysis, as long as the same alleles are being tested. While two different individuals may share identical values for some alleles, only genetically identical twins will share identical values for all alleles. Therefore, if two genetic profiles reflect identical values for one allele, this may or may not reflect that the two profiles were created from tissue derived from one individual. Conversely, if any one allele reflects a different value for the two genetic profiles, then the two profiles were conclusively derived from different individuals. This is called the rule of exclusion. Identity is confirmed only if all alleles tested are identical. Also, the level of confidence of such confirmation is directly proportional to the number of alleles tested.

Returning to step 520, if the values are identical then the process determines if the genetic profiles contain an allele that has not yet been compared 524. If the genetic profiles contain another allele, then the process repeats the comparison for the next allele 518, thereby returning the process to step 512. If the genetic profiles contain no further alleles to be compared, then the process outputs a result indicating that the genetic profiles are identical 522B.

In an alternate embodiment the process described in FIG. 5 continues its analysis for all alleles upon finding a single allele where the values for the two genetic profiles do not match. In this alternate embodiment the inventive process still outputs a negative result 522A upon completing the analysis, but also stores results from each allele compared.

In another alternate embodiment the inventive process compares all corresponding allele values in one simultaneous step.

In yet another alternate embodiment the process described in FIG. 5 includes the ability of the consumer to select at step 510 multiple genetic profiles to be compared against a single genetic profile. In this embodiment the inventive process simply repeats the steps described in FIG. 5 for each additional genetic profile selected to be compared, and outputs results 522 for each comparison.

In yet another alternate embodiment the process described in FIG. 5 includes detailed explanations of the analysis results at step 522, to be downloaded to the consumer's computer. Such detailed explanations of the analysis results include, but are not limited to information regarding the number of skipped alleles 516, reasons for skipping, the number of alleles successfully compared, probabilities of erroneous matches, and other data that may be helpful to the consumer in determining the value of a reported result.

Further expanding upon step 410 from FIG. 4, FIG. 6 is a flow chart representing an exemplary embodiment of the steps taken by the inventive process in performing a comparison of three genetic profiles for confirmation of parentage. For this type of comparison the consumer must first identify the genetic profile that reflects the offspring in question, and the genetic profiles that represent parents in question 602. Step 602 represents a specific exemplary embodiment of step 408 from FIG. 4. A representation of an exemplary web page reflecting a consumer's choices is shown in FIG. 8. At step 604 the inventive process notes the two numerical values for each parent genetic profile for the first allele pair, and notes the two numerical values for the offspring genetic profile at the same allele. In one embodiment 3 database arrays are created to store all allele pairs available for the subjects.

The four combinations of numerical values for the first allele pair, given the two numerical values for each potential parent at the corresponding allele pair, represent classic Mendelian genetic analysis. If the two numerical values for the offspring in question match any of the four possible combinations created by two values from each potential parent at the given allele pair, then it is possible that the offspring in question is the offspring of the two parents in question. If the two values of the offspring in question do not match any of the four possible combinations of values derived from the parents' in question allele pair values from the corresponding allele pair, then the offspring cannot be the offspring of the parents on question. Any one negative result from any allele pair proves that the offspring is not the child of the parents in question. If the offspring is actually the genetic combination of the parents in question then all alleles of the child at each allele will be one of the four possible combinations of the parents' allele pair values. This is the rule of exclusion as it is applied to parentage testing, see paragraph 67.

At step 606 the inventive process checks the array of allele value combinations and offspring allele values within the first allele pair for any null values or values that are outside of pre-set ranges. If any such values exist in the first allele pair, then the inventive process skips the allele 608, and repeats the process 616 for the next allele, thereby returning to step 604. If no values are missing or outside the given ranges, then the inventive process compares the two values for the offspring for the allele in question against the four possible combinations of values created for the parents in question for the given allele pair as described in step 604. If the offspring's two values do not match any of the possible combinations of values for the parents for the given allele pair, then the inventive process stops the analysis and outputs a result to the consumer's computer reflecting that the offspring in question is not the offspring of the parents in question 612A. If the offspring's two values do match any of the possible combinations of values for the parents for the given allele pair, then the inventive process determines if any additional alleles remain to be compared, as described in steps 604, 606, and 610. If one or more alleles remain to be compared, then the process repeats 616, thereby returning to step 604. If all alleles have been compared, then the process outputs a result to the consumer's computer reflecting a result that the offspring is, in fact, the genetic combination of the two parents in question 612B.

In an alternate embodiment the process described in FIG. 6 continues its analysis for all alleles upon finding a single allele where the two values for the offspring at a given allele do not match any of the combinations of values derived from the parents in question at the given allele pair. In this alternate embodiment the process still outputs a negative result 612A upon completing the analysis, but also stores results from each allele compared.

In an alternate embodiment an array is created to store the results from each allele comparison. Table 1 reflects exemplary values that are stored in one alternative embodiment. In an alternate embodiment such results are displayed on the consumer's computer along with the comparison results, thereby giving additional value to the bare comparison result.

TABLE 1

Parentage Test Results
Parentage test results for DN Number: di3305 Status: Ready
Legend

| | |
|---|---|
| n/a | No data sent from the lab for this marker |
| true | Certification Passes: Subject DNA matches parents at a marker, All (non-skipped) markers must be true for a Pass |
| Fail-Dam | Certification Fails: Mismatch on Dam, any Fail-Dam will disqualify the subject |
| Fail-Sire | Certification Fails: Mismatch on Sire, any Fail-Sire will disqualify the subject |
| Fail-Puppy-NoDNA | Marker Skipped: Missing data for the Subject |
| Fail-Dam-NoDNA | Marker Skipped: Missing data for the Dam |
| Fail-Sire-NoDNA | Marker Skipped: Missing data for the Sire |

In another alternate embodiment the process described in FIG. 6 includes detailed explanations of the analysis results at steps 606 and 610, to be downloaded to the consumer's computer. Such detailed explanations of the analysis results include, but are not limited to information regarding the number of skipped alleles 608, reasons for skipping, the number of alleles successfully compared, probabilities of erroneous matches, and other data that may be helpful to the consumer in determining the value of a reported result.

In yet another alternate embodiment test results, individual allele results, and all identifying information shown on the results screen is written to a unique record in the database and permanently maintained as a record of the analysis.

In yet another embodiment the information from the unique record written after comparison is displayed on a screen with the ability to print a certificate. An exemplary certificate is represented in FIG. 10. In one embodiment the certificate is rendered in standard HTML using data from the comparison record, and is designed to print on a standard printer.

In another alternate embodiment a record of all offspring who have had their parents confirmed and certified is maintained on the server to display that status on any public or private screen on the website. The information containing a passed test result and the certified parents is stored in the database table used to identify the offspring. As an exemplary embodiment, the homepage of the DNA World Pet Registry, represented in FIG. 7, contains search functions which can look up any identifying number associated with any subject in the system. Public profiles accessible from this webpage display information for all offspring with confirmed parentage. In the alternate embodiment any genetic profile can be selected regardless of ownership of the profile and can be used as a potential Dam or Sire during parentage analysis without the need to re-collect DNA from those potential parents. Also, once any offspring have been certified it can be used as a potential parent for comparison and confirmation of parentage for a new generation of offspring.

It should be further understood that alternate embodiments of the inventive process are used to compare genetic profiles with compilation genetic profiles where said compilation genetic profiles represent allele values that are known to be associated with specific phenotypic traits. Alternatively, the inventive process can be used to compare genetic profiles with compilation genetic profiles where said compilation genetic profiles represent allele values that are known to be associated with predispositions to specific disease states.

While this invention has been described in detail with particular reference to exemplary embodiments thereof it will be understood that variations and modifications can be effected within the spirit and scope of the invention as described herein.

What is claimed is:

1. A process of remotely and automatically confirming parentage of an offspring comprising the steps of
   a) launching a web browser;
   b) navigating to a web page;
   c) selecting from a database of genetic profiles on said web page a first genetic profile derived from a first genetic analysis performed upon a first tissue sample taken from a first potential parent;
   d) selecting from said database of genetic profiles on said web page a second genetic profile derived from a second genetic analysis performed upon a second tissue sample taken from a second potential parent; and
   e) selecting on said web page a third genetic profile derived from a third genetic analysis performed upon a third tissue sample taken from a potential offspring.

2. A process of automatically comparing two genetic profiles comprising the steps of:
   a) comparing a first value representing an allele of a first genetic profile against a value representing an allele of a second genetic profile;
   b) recording whether the first value is or is not identical to the second value; and
   c) repeating steps a and b for a plurality of values representing a plurality of alleles derived from said first and second genetic profiles.

3. The process of claim 2 wherein the process is performed by a computer.

4. The process of claim 2 wherein the values for the genetic profiles are stored in an electronic database.

5. The process of claim 2 further comprising the steps of
   a) outputting the recorded results of the plurality of comparisons.

6. The process of claim 2 further comprising the steps of
   a) comparing the recorded results of the plurality of comparisons to a known standard; and
   b) recording whether the results of the plurality of comparisons matches the known standard.

7. The process of claim 2 wherein the first and second genetic profiles represent values derived from human tissue samples.

8. The process of claim 2 wherein the first and second genetic profiles represent values derived from equine tissue samples.

9. The process of claim 2 wherein the first and second genetic profiles represent values derived from canine tissue samples.

10. The process of claim 2 wherein the first and second genetic profiles represent values derived from feline tissue samples.

11. The process of claim 2 wherein the process of automatically comparing two genetic profiles is performed remotely via the Internet.

12. The process of claim 2 wherein the first and second genetic profiles represent values derived from different individuals.

13. The process of claim 2 wherein the first and second genetic profiles represent values derived from the same individual.

14. A process of automatically comparing genetic profiles comprising the steps of:
   a) selecting a first genetic profile;
   b) selecting a second genetic;
   c) selecting a third genetic profile;
   d) combining one value from a first allele from the first genetic profile with one value from the second genetic profile thereby creating a first potential offspring allele;
   e) recording the values of the first potential offspring allele;
   f) repeating steps d and e three more times thereby creating a second potential offspring allele, third potential offspring allele, and fourth potential offspring allele;
   g) comparing the values of the first allele from the third genetic profile against the first, second, third, and fourth potential offspring alleles;
   h) recording whether the first allele from the third genetic profile is identical to any one of the first, second, third, and fourth potential offspring alleles;
   i) repeating steps d through h for a plurality of alleles derived from said first, second, and third genetic profiles.

15. The process of claim 14 further comprising the steps of
   a) outputting the recorded results of the plurality of comparisons.

16. The process of claim 14 wherein the first, second, and third genetic profiles represent values derived from human tissue samples.

17. The process of claim 14 wherein the first, second, and third genetic profiles represent values derived from equine tissue samples.

18. The process of claim 14 wherein the first, second, and third genetic profiles represent values derived from canine tissue samples.

19. The process of claim 14 wherein the first, second, and third genetic profiles represent values derived from feline tissue samples.

20. The process of claim 14 wherein the process of automatically comparing three genetic profiles is performed remotely via the internet.

* * * * *